(12) United States Patent
Guérard et al.

(10) Patent No.: US 7,563,287 B2
(45) Date of Patent: Jul. 21, 2009

(54) WRIST PROSTHESIS

(76) Inventors: Jean-Louis Guérard, Rue du Centre 74, St-Sulpice, Vaud (CH) 1025; Léopold Pflug, M75, Lavigny, Vaud (CH) 1175; Daniel Egloff, au de la Gare 9, 1003, Lausanne, VD (CH) CH 1003

( * ) Notice: Subject to any disclaimer, the term of this patent is extended or adjusted under 35 U.S.C. 154(b) by 0 days.

(21) Appl. No.: 10/469,668

(22) PCT Filed: Feb. 27, 2002

(86) PCT No.: PCT/CH02/00115

§ 371 (c)(1),
(2), (4) Date: Sep. 2, 2003

(87) PCT Pub. No.: WO02/069853

PCT Pub. Date: Sep. 12, 2002

(65) Prior Publication Data

US 2004/0073316 A1  Apr. 15, 2004

(30) Foreign Application Priority Data

Mar. 2, 2001  (CH) .................................. 391/01

(51) Int. Cl.
*A61F 2/42* (2006.01)
(52) U.S. Cl. .................. 623/21.13; 623/21.12
(58) Field of Classification Search .... 623/21.11–21.19
See application file for complete search history.

(56) References Cited

U.S. PATENT DOCUMENTS

| 3,708,805 | A | * | 1/1973 | Scales et al. | 623/20.12 |
|---|---|---|---|---|---|
| 3,909,853 | A | * | 10/1975 | Lennox | 623/21.13 |
| 4,100,626 | A | | 7/1978 | White | |
| 4,193,139 | A | * | 3/1980 | Walker | 623/21.17 |
| 4,229,840 | A | | 10/1980 | Gristina | |
| 4,229,841 | A | * | 10/1980 | Youm et al. | 623/21.12 |

(Continued)

FOREIGN PATENT DOCUMENTS

EP  0214773 A  3/1987

(Continued)

OTHER PUBLICATIONS

English translation of FR 2 590 794 A1 (previously cited by the Examiner).*

*Primary Examiner*—Alvin J Stewart
*Assistant Examiner*—Javier G. Blanco
(74) *Attorney, Agent, or Firm*—Clifford W. Browning; Krieg DeVault LLP

(57) ABSTRACT

The invention concerns a wrist prosthesis wherein the surfaces of the spherical caps of the base plates of the lateral rods are pressed against the corresponding concave surfaces of the seat under the action of the spindle made of elastic material maintained in extension between the two pairs of half-locks. Each of the pairs of semi-cylindrical elements is maintained assembled by being engaged from outside inwards in the central passage of one of the rods and locks one of the cylindrical ends of the central part of the spindle. The central rod is engaged by its shaft in a transverse blind bore of the seat and the groove provided in the flanks of its slot is clipped on the rim of the spindle.

17 Claims, 3 Drawing Sheets

U.S. PATENT DOCUMENTS

Figure 3:
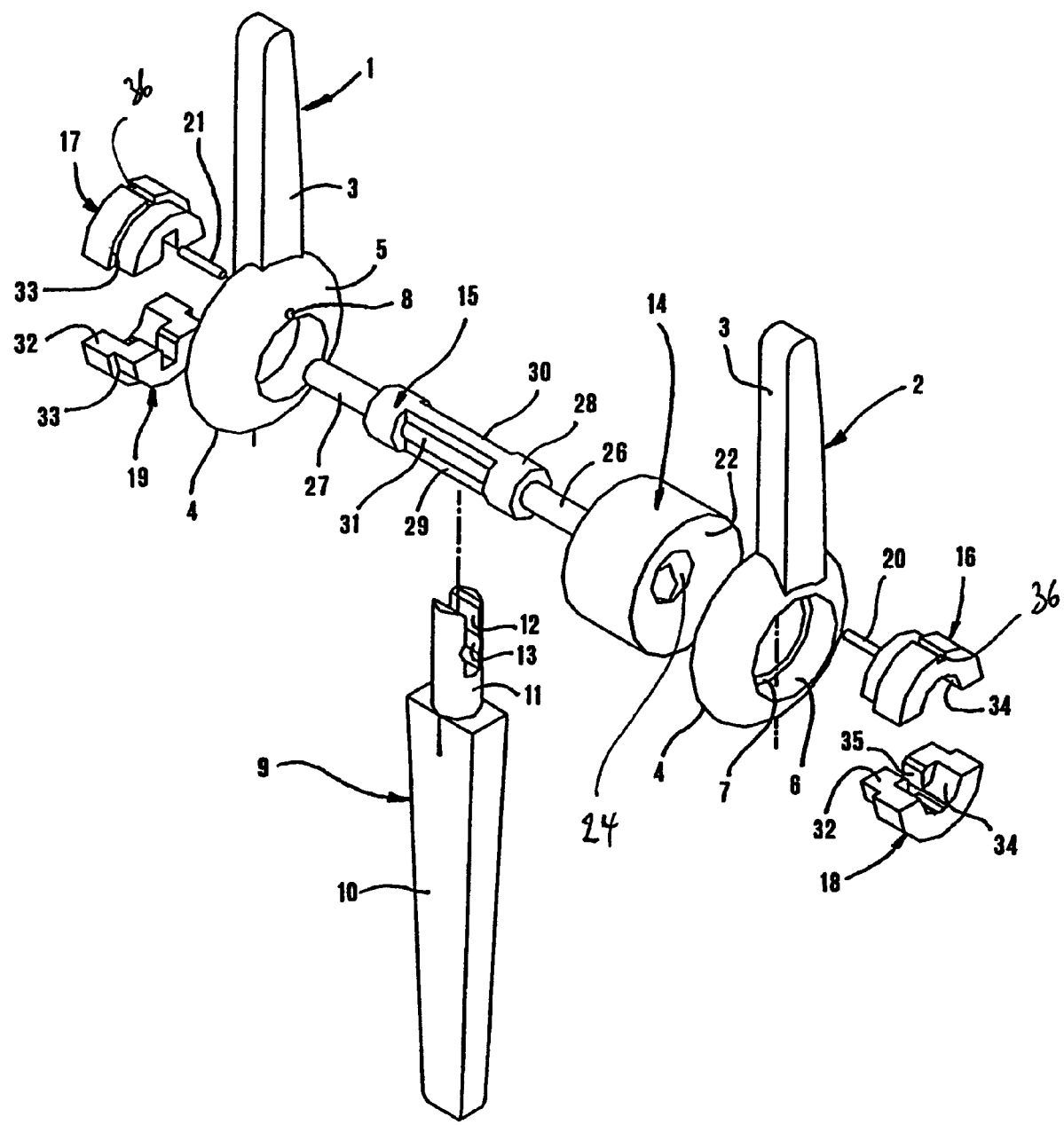

| | | | |
|---|---|---|---|
| 4,307,473 A | 12/1981 | Weber | |
| 4,714,476 A | 12/1987 | Ranawat | |
| 5,314,484 A * | 5/1994 | Huene | 623/20.12 |
| 5,458,647 A * | 10/1995 | Brochier et al. | 623/21.17 |
| 6,699,290 B1 * | 3/2004 | Wack et al. | 623/20.12 |

FOREIGN PATENT DOCUMENTS

| | | | |
|---|---|---|---|
| EP | 0454645 A | 10/1991 | |
| FR | 2590794 A1 * | 6/1987 | |
| FR | 2669214 A | 5/1992 | |
| FR | 2681240 A | 3/1993 | |
| WO | WO9522945 A | 8/1995 | |
| WO | WO9857600 A | 12/1998 | |

* cited by examiner

FIG.1
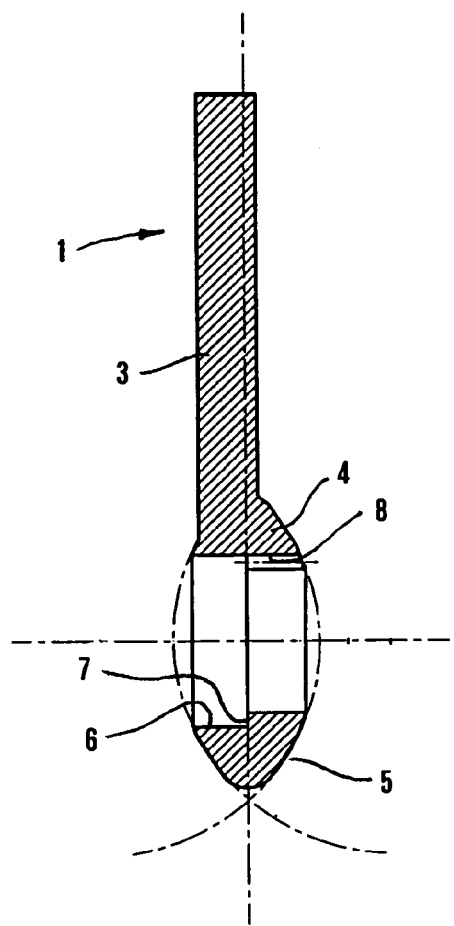
FIG.2
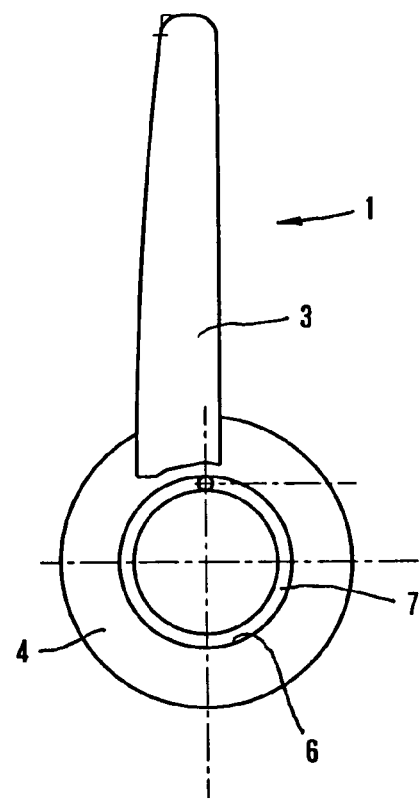
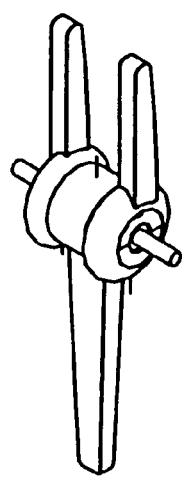
FIG.7

FIG.5

WRIST PROSTHESIS

The object of the present invention is a wrist prosthesis comprising a plurality of rigid rods including a central rod intended to be anchored in the radius and two lateral rods intended to be anchored in metacarpals and an articulation mechanism connecting the said rods. Prostheses of this type have already been described, in particular in the French patent application publications Nos 2681240 and 2669214, in which the functions which the articulation mechanism must fulfill are explained. In the technical field of wrist prostheses it is obviously sought to provide medical science with devices which enable the patients to perform, with the wrist and fingers, movements which are as easy and varied as possible, with satisfactory comfort.

The wrist prostheses known at the present time have structures which are either too loose or too rigid and are often subject to loosening. It is consequently necessary to replace them, generally at very short intervals.

The aim of the present invention is to propose a wrist prosthesis which on the one hand remedies the known prostheses problems and on the other hand better allows natural wrist movements, and with greater comfort.

To this end, the present invention concerns a wrist prosthesis comprising a plurality of rigid rods, including a central rod intended to be anchored in the radius and two lateral rods intended to be anchored in metacarpals, and an articulation mechanism connecting the said rods, characterised in that the articulation mechanism comprises three elements, secured respectively to the lateral rods and central rod, assembled elastically so as to allow movements of the lateral rods with respect to the central rod and relative movements of the lateral rods with respect to each other.

According to one embodiment of the said wrist prosthesis, the said articulation mechanism comprises a seat made from a rigid material with two front faces, a spindle made from an elastically deformable and extensible material, engaged in a central opening in the seat, each of the lateral rods comprising a base comprising a transverse passage, the said bases having front surfaces with shapes conjugate with those of the front faces of the seat, the spindle being held in extension by locking of its ends in the transverse passages in the bases by locks so that the said front faces of the bases are pressed against the front faces of the seat so as to constitute articulations of the swivel type allowing limited relative movements of the lateral rods with respect to the seat.

The said front faces of the seat can be concave in shape, the said front faces of the bases having the form of spherical caps. According to a variant, the said front faces of the seat are convex in shape, the said front faces of the bases being convex in shape.

The central rod can be engaged by one end in a transverse bore provided half-way along the length of the seat and can have at the said end a slot which straddles the central part of the spindle; the central part of the spindle and the slot in the central rod can have corresponding profiles arranged to provide the fixing of the said rod with respect to the spindle.

The seat can be cylindrical in shape, the central rod being rectilinear and disposed radially with respect to the axis of the seat and the lateral rods comprising a rectilinear jamb secured to the base and offset laterally with respect to the axis of the base.

The bases of the lateral rods can be annular in shape with a central passage provided with an internal shoulder intended to retain a locking device which fixes in the base one of the ends of the spindle whilst keeping the latter in extension.

Each locking device can be formed by two half-locks kept clamped against each other by their engagement in the said central passage and held in abutment against the said shoulder by the traction of the spindle; the locking devices can be locked against any rotation movement with respect to the base which contains them by a pin passing through the base and one of the half-locks.

Figure 6:
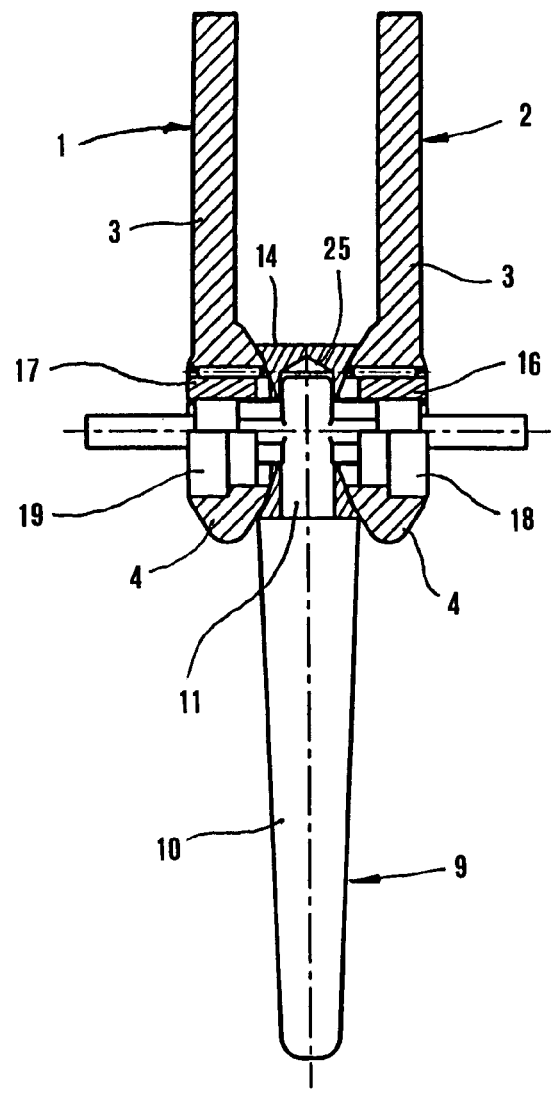
Figure 4:
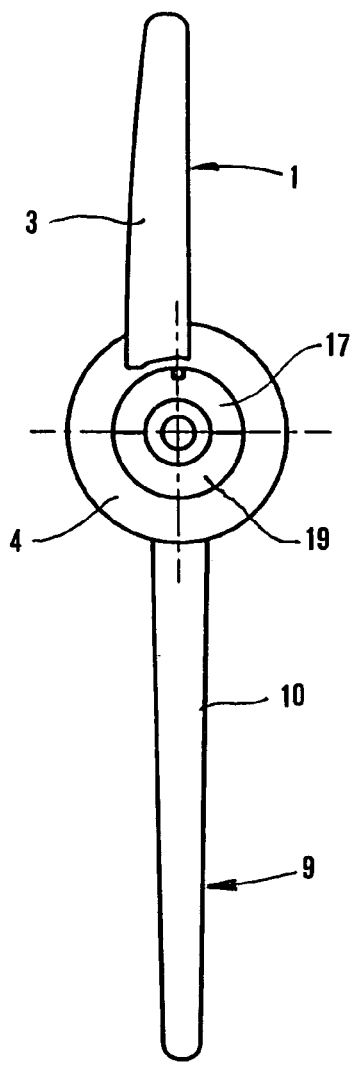

A description is given below, by way of example, of an embodiment of the wrist prosthesis according to the invention with reference to the accompanying drawing, where:

FIG. 1 is a view in section of a lateral rod of the prosthesis,

FIG. 2 is an elevation view, in the direction of the arrow A, of the rod of FIG. 1, FIG. 3 is an exploded perspective view of the various constituents of the prosthesis, FIG. 4 an elevation view of the whole of the prosthesis in the assembled state, FIG. 5 a plan view from above of the prosthesis of FIG. 4, FIG. 6 a view in section along the line 6—6 in FIG. 5 showing all the constituents of the prosthesis, and FIG. 7 is a perspective view of the prosthesis in the assembled state.

The prosthesis is composed essentially of three rigid rods, including two lateral rods 1 and 2 and a central rod 9, assembled so as to be mobile with respect to each other. FIGS. 1 and 2 depict the lateral rod 1 which is symmetrical with the rod 2 and formed from a single metallic piece or from plastics material, shaped by casting, moulding or machining. This piece comprises a rectilinear jamb 3, rectangular in cross-section (or any other suitable shape, such as polygonal, circular or oval), having a profile slightly tapered from a base 4. This part 4 of the rod 1 is annular in shape seen in elevation (FIG. 2) and ovoid in shape seen in section (FIG. 1). In particular the front face 5 situated opposite to the one which is visible in FIG. 2 is a portion of a spherical surface treated so as to be perfectly even and smooth. The base of each of the lateral rods fulfils the role of a swivel. The central opening in the annular base 4 is a cylindrical passage 6 which has an internal shoulder 7, the rear part of the passage 6 having a diameter slightly greater than the front part. A bore 8 whose diameter is equal to the width of the shoulder 7 is provided along the top generatrix of the passage 6, in the front zone having the smallest diameter.

Looking at FIG. 2 it can be seen that the jamb 3 is placed in a position slightly offset with respect to the vertical axis passing through the centre of the base 4. For the lateral rod 2, which has the same shape and same general constitution as the rod 1, this offset of the jamb 3 is symmetrical with respect to what is shown in FIG. 2, as will also be seen below.

The two rods 1 and 2 are depicted in FIG. 3 in positions similar to those which they occupy in the mounted prosthesis and it can be seen that they face each other, the surface 5 of the piece 1 being visible in FIG. 3 whilst this same surface 5 is concealed with regard to the piece 2.

The third rod 9 is also visible in FIG. 3. It comprises a jamb 10 with a rectangular cross-section decreasing towards the bottom and which is extended upwards by a cylindrical journal 11 in which a slot 12 is milled, with parallel flanks, interrupted half-way up by a transverse groove 13.

The mechanical means provided for assembling and adjusting the three rods 1, 2 and 9 with respect to one another consist of a seat 14, a spindle 15, two pairs of half-locks 16, 17, 18 and 19, and two pins 20 and 21, each allocated to one of the half-locks in each pair.

It should be stated that the drawing in FIG. 3 was obtained by means of a drawing program ill-suited to the representation of the curves, which are drawn in the form of polygonal lines. In reality, the external shape of the pieces 17, 19, 4, 27, 15, 28, 26, 14, 16 and 18 is circular, as are the passages which pass through them.

The seat 14 is a piece with a cylindrical external shape, with two end faces 22, 23 in the form of portions of concave spherical surfaces, exactly fitted so as each to receive the face 5 of one of the rods 1 or 2. It is pierced along its axis by a cylindrical passage 24 and finally has a blind bore 25 (FIG. 6) which passes through it from bottom to top vertically to a point close to its external peripheral surface. The diameter of this bore is sufficient to give passage to the journal 11 on the central rod 9, the groove 13 coming to be placed at the centre of the cylindrical passage 24.

The seat can be produced from synthetic material, for example from implantable polyethylene having a good slip surface.

According to one variant, the seat can be produced with convex end faces 22, 23. In this case, the bases 4 of the rods 1 and 2 will be produced with concave front surfaces 5 arranged to correspond to the convex surfaces of the end faces of the seat, so as to enable articulations of the swivel type to be produced.

The spindle 15 is the essential piece of the entire assembly mechanism. This piece is made from elastomer or other flexible synthetic material having the required degrees of stability and elasticity. Its general shape is cylindrical with two stems 26, 27 at its ends, and between these stems a cylindrical central part 28 whose diameter is such that it enters the cylindrical passage 24 in the seat 14, and which has two scallops 29 and 30 with flat parallel bottoms and an elongate protrusion 31 at the centre of each bottom of a scallop. The distance between the parallel bottoms of the scallops is equal to the width of the slot 12 and the radii of the protrusions 31 correspond to that of the groove 13. It can be seen in FIG. 3 that the journal 11 of the rod 9, by engaging on the central part of the spindle 15, is snapped onto the protrusions 31 and will be held in place by the elasticity of the material of the spindle 15.

The elasticity of this material also provides the clamping of the spherical faces 5 of the rods 1 and 2 against the concave faces 22 and 23 of the seat 14. For this purpose the stems 26 and 27 serve as traction means for effecting an extension of the cylindrical part 28 of the spindle 15 so as to allow the fitting of the pairs of half-locks 16, 18 and 17, 19.

The half-locks 16, 18 and 17, 19 are pieces in the form of arcs of a cylinder delimited by a flat face 32 so that two homologous half-locks (for example 16, 18) placed one against the other with their flat faces 32 in contact form a cylindrical body with two stages with different diameters, separated by a shoulder 33. Internally each assembly of two homologous half-locks has a cylindrical hollow 34 with, in its bottom, a profiled opening 35 whose dimensions correspond to the profile of the scalloped central part of the spindle 15. Thus, in particular, in each half-lock, the angles between the flat face 32 and the edges of the rectangular scallop 35 are bevelled so as to correspond with the protrusion 35 on the spindle 15. Finally, the two half-locks 16 and 17 have, in their external lateral face, at the top part thereof, a groove 36 parallel to the spindle and whose diameter corresponds to that of the pins 20 and 21.

FIGS. 4, 5, 6 and 7 show how the prosthesis is in its assembled state. The elasticity of the spindle 15 keeps the two lateral rods 1 and 2 and the central rod 9 connected to the seat 14 whilst allowing them various movements. The spindle 15 being in extension, the end flanks of the scallops 29 and 30 are attached to the edges of the scallops 35 in the bottoms of the hollows 33 in the locks 16/18 and 17/19, which are themselves engaged in the passages 6 in the bases 4 of the rods 1 and 2. The spherical faces 5 of the bases 4 are therefore kept pressed against the concave faces 22 and 23 of the seat 14, whilst the journal 11 of the central rod 9 is engaged in the blind hole 25 in the seat, the central part of the cylindrical area 28 of the spindle 15 extends in the slot 12 and the protrusions 31 are engaged in the grooves 13. The pins 20 and 21 rotationally secure the locks 16/18 and 17/19 each to the lateral rod 1 or 2 with which it is associated.

This arrangement allows rotation movements of the rods 1 and 2 with respect to the seat 14 about the axis of the latter and certain pivoting movements of the rods 1 and 2 about axes perpendicular to that of the seat. It also allows rotation movements of the central rod 9 about its own axis, because the scallops 29 and 30 have a length greater than the diameter of the journal 11 (see FIG. 6).

FIGS. 3, 5 and 6 depict the spindle 15 still provided with its stems 26 and 27, but it is important to note that these elements fulfill only an ancillary function at the time of mounting of the prosthesis and will be cut after fitting.

This is because, in order to perform the mounting operation with the elements described, one of the pairs of half-locks, the lateral rod, the seat and the spindle will be assembled, the two half-locks being pressed against each other, so as to enclose between them the corresponding cylindrical end of the central part 28 of the spindle 15. Next, the other lateral rod will be fitted, the spherical surface 5 of its base being placed in contact with the corresponding concave face of the seat. The spindle 15 then being put in extension by traction on the stems 26, 27, so that the other cylindrical end of the central part 28 of the spindle appears on the outside of the passage 6 of the second lateral rod, the second pair of half-locks can be engaged on each side of the projecting part of the spindle and are clamped so as to enclose in the hollow 34 the other end of the central part 28 of the spindle 15. Finally, it suffices to release the tension on the stems 26/27 so that the assembly is in place. The central rod 9 can be engaged in the transverse bore 25 in the seat 14, the journal 11 being fixed by its groove 13 on the protrusion 31 of the spindle.

These operations being executed, the stems 26/27 are no longer of any use and can be cut.

The prosthesis according to the present invention makes it possible to better reproduce the mobility of the bones with respect to each other than the prostheses of the prior art, particularly by virtue of its flexibility due to the various degrees of freedom which it allows in combination with the elastic properties of its spindle 15, which, with each degree of freedom, associates a corresponding return force.

The main degrees of freedom allowed by the prosthesis according to the invention are as follows:
rotation of the rods 1 and 2 about the spindle 15
lateral pivoting of the rods 1 and 2, with possible detachment of their bases 4 with respect to the seat 14 in the event of extreme movement
longitudinal axial movement of the rod 9.

The invention claimed is:

1. Wrist prosthesis comprising a plurality of rigid rods, including a central rod intended to be anchored in the radius and two lateral rods in two separate pieces intended to be anchored in metacarpals, and an articulation mechanism connecting the said rods, wherein said articulation mechanism comprises three rigid elements, a first one of which is connected to the central rod, the second and third ones of which are rigidly secured respectively to one of said lateral rods, said articulation mechanism further comprising means for elastically assembling said elements so as to allow movements of said rods when anchored in the radius and metacarpals, respectively, these movements comprising movements of the lateral rods with respect to the central rod and relative movements of the lateral rods with respect to each other, wherein the first element of said articulation mechanism is a seat made from a rigid material with two front faces and with a transverse bore, the second and third elements respectively are each a base of said lateral rods, wherein each base of said lateral rods comprises a transverse passage and a front surface, and wherein the mechanism further comprises a spindle made from an elastically deformable and extensible material with a central part traversing said transverse bore of the seat and two ends each traversing one of said transverse passages of the bases, said spindle being held in extension by locking of said ends in the transverse passages in the bases by locks so that the said front surfaces of the bases are pressed against the front faces of the seat so as to constitute articulations of the swivel type allowing limited relative movements of the lateral rods with respect to the seat.

2. Prosthesis according to claim 1, wherein the said front faces of the seat are concave in shape, the said front surfaces of the bases having the form of spherical caps.

3. Prosthesis according to claim 1, wherein the said front faces of the seat are concave in shape, the said front surfaces of the bases being convex in shape.

4. Prosthesis according to claim 1, wherein the central rod is engaged by one end in a transverse bore provided half-way along the seat and has at the said end a slot which straddles the central part of the spindle.

5. Prosthesis according to claim 4, wherein the central part of the spindle and the slot in the central rod have corresponding profiles arranged so as to provide the fixing of the said rod with respect to the spindle.

6. Prosthesis according to claim 1, wherein the seat is cylindrical in shape, the central rod is rectilinear and disposed radially with respect to the axis of the seat and each of the lateral rods comprise a rectilinear jamb fixed to the base and said jamb is offset laterally with respect to the axis of the base.

7. Prosthesis according to claim 1, wherein the bases of the lateral rods are annular in shape with a central passage therein provided with an internal shoulder intended to hold a locking device which fixes in the base one of the ends of the spindle whilst keeping the latter in extension.

8. Prosthesis according to claim 7, wherein each locking device is formed by two half-locks kept clamped against each other by their engagement in the said central passage and held in abutment against the said shoulder by the traction exerted by the spindle.

9. Prosthesis according to claim 8, wherein the locking devices are locked against any rotation movement with respect to the base which contains them by a pin passing through the base and one of the half-locks.

10. Prosthesis according to claim 1, wherein the bases of the lateral rods are annular in shape with a central passage therein provided with an internal shoulder intended to hold a locking device which fixes in the base one of the ends of the spindle whilst keeping the latter in extension.

11. Prosthesis according to claim 1, wherein the seat is cylindrical in shape, the central rod is rectilinear and disposed radially with respect to the axis of the seat and each of the lateral rods comprise a rectilinear jamb fixed to the base and said jamb is offset laterally with respect to the axis of the base.

12. Prosthesis according to claim 11, wherein the bases of the lateral rods are annular in shape with a central passage therein provided with an internal shoulder intended to hold a locking device which fixes in the base one of the ends of the spindle whilst keeping the latter in extension.

13. Prosthesis according to claim 1, wherein the central rod is engaged by one end in a transverse bore provided half-way along the seat and has at the said end a slot which straddles the central part of the spindle.

14. Prosthesis according to claim 13, wherein the seat is cylindrical in shape, the central rod is rectilinear and disposed radially with respect to the axis of the seat and each of the lateral rods comprise a rectilinear jamb fixed to the base and said jamb is offset laterally with respect to the axis of the base.

15. Prosthesis according to claim 14, wherein the bases of the lateral rods are annular in shape with a central passage therein provided with an internal shoulder intended to hold a locking device which fixes in the base one of the ends of the spindle whilst keeping the latter in extension.

16. Prosthesis according to claim 15, wherein each locking device is formed by two half-locks kept clamped against each other by their engagement in the said central passage and held in abutment against the said shoulder by the traction of the spindle.

17. Prosthesis according to claim 16, wherein the locking devices are locked against any rotation movement with respect to the base which contains them by a pin passing through the base and one of the half-locks.

\* \* \* \* \*